(12) United States Patent
Wang et al.

(10) Patent No.: US 10,172,443 B2
(45) Date of Patent: Jan. 8, 2019

(54) ORAL CARE TOOLS AND SYSTEMS

(71) Applicants: Yong-jing Wang, Suzhou (CN); Ethan Daniel Schur, San Francisco, CA (US)

(72) Inventors: Yong-jing Wang, Suzhou (CN); Ethan Daniel Schur, San Francisco, CA (US)

( * ) Notice: Subject to any disclaimer, the term of this patent is extended or adjusted under 35 U.S.C. 154(b) by 285 days.

(21) Appl. No.: 14/455,932

(22) Filed: Aug. 10, 2014

(65) Prior Publication Data

US 2015/0044629 A1  Feb. 12, 2015

Related U.S. Application Data

(60) Provisional application No. 61/864,620, filed on Aug. 11, 2013.

(51) Int. Cl.
*A61C 17/22* (2006.01)
*A46B 15/00* (2006.01)
*A61C 19/04* (2006.01)
*A61C 15/04* (2006.01)
*A61C 17/02* (2006.01)

(52) U.S. Cl.
CPC ...... *A46B 15/0006* (2013.01); *A46B 15/0008* (2013.01); *A46B 15/0012* (2013.01); *A46B 15/0038* (2013.01); *A46B 15/0044* (2013.01); *A61C 19/04* (2013.01); *A61C 15/046* (2013.01); *A61C 17/0202* (2013.01)

(58) Field of Classification Search
CPC ....... A61C 15/047; A61C 17/16; A61C 17/20; A61C 17/22; A46B 15/0006; A46B 15/0008; A46B 15/0038
See application file for complete search history.

(56) References Cited

U.S. PATENT DOCUMENTS

2012/0295216 A1* 11/2012 Dykes .................... A61C 19/04
433/27

FOREIGN PATENT DOCUMENTS

WO   WO 2010134050 A1 * 11/2010  ............. A61C 17/00

* cited by examiner

*Primary Examiner* — Julianna N Harvey (57) ABSTRACT

The present invention is directed to oral care systems having an oral care tool and a first software application. The oral care tool includes a cleaning module, a sensing module, and a communications module. The first software application is run on a computing device, such as a mobile computing device, that receives the data from the sensing module and reproduces a simulated image reflecting the result of brushing. The mobile computing device can be linked to a cloud server that receives data from the first software application and saves detailed brushing data for each user. The first software application visualizes brushing and transforms brushing into a fun game. The cloud server collects and stores the detailed brushing data and provides it to users and care providers.

19 Claims, 7 Drawing Sheets

ORAL CARE TOOLS AND SYSTEMS

This application claims priority of U.S. Provisional Patent Application No. 61/864,620, filed Aug. 11, 2013, the entire contents of which are incorporated herein by reference.

TECHNICAL FIELD

The invention generally pertains to oral care systems, and more particularly to smart tooth brushing systems that visualize the brushing process and provide users real time visual feedback to improve their brushing.

BACKGROUND OF THE INVENTION

Tooth brushing is a blind process. People can't see what they are doing inside of their mouth and cannot see the results of brushing. Therefore they do not know whether they are brushing properly. Tooth brushing is considered a boring chore for many children and adults.

There are several ways to address this problem. The first one is to add an endoscope at the head of the toothbrush. The endoscope takes pictures and displays them for the users. This method is difficult to implement due to bubbles, water, and toothpaste making it very difficult to detect an acceptable image of the teeth during brushing.

The second way is to add sensors in the tooth brush head as Park disclosed in U.S. Pat. No. 7,976,388. Park disclosed an oral care system integrating temperature sensors or movement, direction or acceleration sensors in a toothbrush. Rating or audio feedback is provided based on the data detected from the sensor. However, Park does not disclose any way to visualize the brushing process and let people see their brushing results in real time. Furthermore, it is difficult for current sensor technology to detect absolute position data. Thus Park's patent has not disclosed any way to detect where people are brushing. It is impossible to visualize the brushing process without knowing this key information.

As a result, there exists a current need for oral care tools and related systems that can provide a real time image of the brushing result to the user and provide fun for the users when they are brushing.

SUMMARY OF THE INVENTION

In one aspect, the present invention provides an oral care system that induces an oral care tool and a first software application.

The oral care tool can include a cleaning module, a sensing module, and a communications module. The cleaning module is designed to interface with the teeth. The cleaning module could be a brushing head with bristles, a gum stimulator, flossing tool, water flossing tool, tongue scraper, or any other dental tool.

The sensing module includes at least one sensor that generates data, including data about the position of the cleaning module within the oral cavity. The sensing module can also include one or more sensors that detects the type of cleaning module being used with the oral care tool.

The sensing module can be comprised of multiple sensors (e.g., two, three, or more sensors). Examples of such sensors include 3-axis accelerometers, magnetometers, gyroscopes, pressure sensors, load sensors, and Hall Effect sensors. The sensing module can include biochemical sensors.

Typically, the sensing module is attached (directly or indirectly) to the cleaning module. Alternatively, the sensing module can be located on separate computing device, such as a smart watch, ring, or bracelet.

The position of the cleaning module within the oral cavity can be determined by calibrating the oral care tool. Such calibration can be used to map the mouth of a user of the oral care tool. Calibration can be achieved, for example, by pushing a button on the oral care tool when the cleaning module is facing the central incisors of the user. This will set a reference angle (A1). Then the brush care be moved to the most toner molar and the button pressed again, setting a second reference angle (A2). The total length form the central incisors to the most inner molar is L. By repeating the process in different areas of the mouth (e.g., in each quadrant of the mouth), a three dimensional map of the mouth can be generated that can be used to determine the approximate location of the cleaning module within the oral cavity. The position of teeth not involved in the calibration process can be determined by measuring the angle (A) of the oral care tool during operation. The position of such teeth (I) can be calculated by the following equation:

$$I=L*A/(A2-A1).$$

In some cases, the user of the oral care tool may be missing one or more teeth. In such a case, the position of the cleaning module can be determined to be at the location were the missing tooth would have been.

The orientation of the oral care tool (and/or the cleaning module) can determine which face of the teeth the cleaning module is directed towards. This way the cleaning module can be determined to be in any location such as the front side of the central incisors, the top part of the molars, or the back side of the lower molars.

The sensing module also measures the duration that the cleaning module is in each position and orientation within the oral cavity. By adding up all durations, the total time the oral care tool is in use for a particular usage session can be calculated.

The communications module receives the data produced by the sensing module and transmits the received data to a computing device set up to run the first software application. The communications module could be a Bluetooth compatible radio transmitter, a WiFi Direct module, RF4CE, or any other type of wireless communication module.

The computing device can be a mobile computing device, such as a smartphone, tablet, laptop, pica projection computer, smartwatch or similar device. Alternatively, the computing device can be integrated with a smart mirror technology, wherein a reflective mirror doubles as a digital display screen.

The mobile computing device receives the data from the communications module on the oral care tool and reproduces a simulated image that reflects the result of brushing in real time. In general, real time refers to response times of approximately 500 milliseconds or less. However, delays due to interference or other common bottlenecks in the wireless protocol or display system system may result in delay times greater than 500 milliseconds, Preferably, the delay is no longer than one second.

The software application can direct the mobile computing device to upload the data from the oral care tool to a cloud storage system. Thus, in some embodiments, data stored on a cloud storage system can be considered a part of an oral care system of the invention. The cloud server system provide access to the data from the oral care tool to other software applications and/or users of the oral care system. For example, the data from the oral care tool (e.g., accessible from the computing device or cloud storage system) can be used to track oral care and/or aid dental diagnosis.

The first software application can provide a simulated image that includes a visual representation of teeth surfaces within the oral cavity and/or an image of an oral care tool. For example, in some embodiments, the first software application displays representation of the oral care tool at a desired orientation to guide the user. In some embodiments, the first software application tracks total usage of an oral care tool (or cleaning module) and provide a visual representation of the oral care tool (or cleaning module) that changes with increasing usage. In some embodiments, the first software application can optionally compare a detected oral care pattern with a desired oral care pattern. Based on the difference between the detected and desired oral care pattern, the first soft rare application can provide a score for the detected oral care pattern. The detected oral care pattern can be, e.g., a brushing pattern. In some embodiments the first software application tracks total usage of the cleaning module. In such embodiments, a scoring parameter within the first software application can be altered with increasing usage.

The first software application can also provide a game theme. The game theme may or may not include a visual representation of teeth surfaces within the oral cavity and/or an oral care tool. Regardless the positions within the game theme are designed to have a one to one correlation with teeth surfaces within the oral cavity.

The simulated image generated by the first software application can be altered by data provided by the sensors. For example, one or more colors in the simulated image can change based on the provided data. Such changes can highlight important information, such as problems in an oral care pattern (e.g., brushing pattern) and/or the deterioration of an oral care tool (and or cleaning module) due to extended use. The first software application can further allow different users to compete with one another. For example, users can compete remotely or by using a common computing device (e.g. mobile computing device) that is running the first software application. In some embodiments of the invention, the first software application adjusts its routines in an automated manner (e.g., to provide improved guidance on oral care) or in response to manual input. The manual input can be provided to the oral care tool, the computing device, or from another device (e.g., a device connected with the cloud storage system).

The oral care systems of the invention can include a second software application. The second software application can be, for example, capable of running on the device running the first software application or some other device. The second software application can allow for tracking of the usage and performance (e.g., a single usage and/or overall performance) of the oral care tool.

Users of the oral care systems of the invention can include an individual that uses the oral care system to clean (e.g., brush or floss) his or her teeth. Users of the oral care system can also include a parent of a child who uses an oral care system of the invention, or a spouse of a person who uses an oral care system of the invention. Other users of the oral care systems of the invention include care providers, such as a dentist that makes use of the sensor data from the oral care tool to make recommendations on oral care. The recommendations can be provided remotely, e.g., through a second software application that accesses the data from the oral care tool (e.g., the data as stored in a cloud server system), or directly (e.g., verbally). The recommendation or any other user input can modify the operation of the first software application. Such modification can lead to improved guidance that enhances the overall oral care provided by the systems of the invention.

In another aspect, the invention provides methods for improving oral care. The methods include using an oral care system of the invention as part of an oral care routine. As discussed above, an oral care system of the invention can provide guidance on how to improve oral care. As an example, the oral care systems can guide users toward an improved brushing pattern.

In yet another aspect, the invention provides methods for monitoring oral care. The methods include monitoring a person's use of an oral care system and/or the person's oral care performance. The method can be practiced by the person using the oral care tool (e.g., self-monitoring) or by someone associated with the user of the oral care tool (e.g., a parent, spouse, or care provider). The monitoring can be performed remotely (e.g., by accessing data stored in a cloud storage system) or directly (e.g., by accessing the first software application on the computing device).

Additional embodiments of the oral care systems of the invention will be apparent from the detailed description and claims that follow. Those skilled in the art appreciate that the concepts and specific embodiments disclosed herein can be modified, such as by designing different simulated images and/or other games), while carrying out the same essential purposes of the present invention. Such equivalent constructions are encompassed by the oral care systems of the invention.

DETAILED DESCRIPTION OF THE INVENTION

The main goal of present invention is to use sensor technology to detect the position of a cleaning module in the mouth, as well as the cleaning module orientation, stroke velocity, and duration, and visualize these in a simulated image to provide guidance for users. The similar concept can be used to visualize many other processes. A toothbrush will be used as an example of the oral care tool, but a similar concept applies to other oral care tools.

The sensors include but are not limited to gyroscope, magnetometer, accelerometer, temperature meter, strain gauge, load sensor, altimeter, and photo sensor. A timer necessary to measure the real brushing time. A timer should be physically located in the oral care system or use the timer function in the portable computing device like a smartphone, smartwatch, or a tablet.

The gyroscope, magnetometer, and accelerometer can work together to detect rotation angles, i.e. Roll, Pitch and Yaw and quaternion angles of the oral care tool. Roll and Pitch angles are used to determine the brushing surface and brushing angle of the teeth.

The rotation angle of the oral care device can be detected very accurately using sensor technology. Its absolute position is difficult to detect. In one embodiment of the present invention, the Yaw angle is detected first. Because of the curvature of teeth, the Yaw angle is translated to absolute position information of the brushing. The home position is the position of the central incisors. When Users are brushing the central Incisors, the Yaw angle of the brush is ZERO degrees. When users are brushing the most inner Molar, the Yaw angle is at the maximum angle for that user. The Yaw angle of all other teeth can be interpolated using an appropriate equation (e.g., a liner equation). By detecting the Yaw angle, we can detect all the teeth that are brushed.

The reading from a photo sensor can be used to determine the brushing position too. The maximum light generally happens when users are brushing the central incisors. The minimum light happens when users are brushing the most inner molar.

The positional information of the oral care tool relative to the upper and lower rows of teeth is necessary to fully reproduce the simulated image of brushing. In one embodiment of the present invention, the software displays a virtual brush at the upper teeth or lower teeth first and shows a simulated guide image. The user instinctively follows the guidance to brush accordingly at the upper teeth or lower teeth. In another embodiment of present invention, a load sensor or strain gauge is located at or near the head of the brush. The sensor detects force direction and determines if the oral care device is positioned at the upper or lower teeth. Clearly defined rotational gestures can also be used to determine if the cleaning module is positioned at the upper or lower teeth. When users are brushing upper teeth, the upper lip will push the brush head downward. When users are brushing the lower teeth, the low lip will push the brush head up.

In another embodiment of the present invention, one or more photo sensors are placed at an upper edge of the brush head. When users are brushing the upper teeth, the upper lip will block the light therefore the reading from the photo sensor can be used to determine upper or lower teeth are brushing. The level and direction of light may be different depending on the position of the cleaning module. Another photo sensor could be placed at a lower edge of the brush head. These two sensors can work together to give a more accurate information.

The brushing force can be determined in different ways. In one embodiment of present invention, the acceleration is detected by an accelerometer. The brushing force is calculated from the acceleration and the mass of the brush. In another embodiment, a force or load sensor is used to detect the force directly.

All the information from the sensors is wirelessly transferred to a dedicated device or a shared device, like a smartphone or tablet. This device is a main controller of the whole system. We will use a smartphone as an example in the following implementations of the present invention. A similar principle is applicable to other portable devices, like a tablet or a dedicate device.

The smartphone collects all the data from the sensors. The software inside the smartphone reconstructs a simulated image of the brushing processing. Initially, a real or simulated image of a user's teeth is displayed. Some indicators that mimic the plaque and food residue are placed on the image. The software displays a brush at certain location and orientation according to the data from the sensors. The virtual brush moves in real time following the movement of the real cleaning module the user is using. The correlation of the virtual brush with the cleaning module is based on the position of the cleaning module within the oral cavity. The indicators are removed or manipulated based on the brushing strength or efficiency. The brushing strength and efficiency are calculated from the time, brushing position, brushing angle, stroke velocity, and data from the sensors.

In another embodiment of the present invention, a game theme is displayed instead of an image of the user's teeth. Different locations in the game theme are correlated with different teeth. A game weapon or tool is displayed to mimic the cleaning tool (e.g., tooth brush). The game weapon follows the movements of the brush. Game characters like monsters appear at different locations. The user uses tooth brush to control the game weapon to destroy the monster. The monster appears in certain location and at certain frequency according to optimal or improved tooth brushing requirements.

In another embodiment, the game displays the brush at a designated orientation. The user will follow the guidance to achieve better brushing activity. The game compares the detected brushing behavior and the desired behavior to give a score for brushing. The detected brushing behavior could be cumulative, or from one single brushing session. The desired behavior could be based on dental recommendations.

The game can include a scoring parameter which estimates what the final score can be. This parameter can be based on duration and stroke velocity, as well as orientation of the cleaning module. It can also be based on the total usage lifetime of the cleaning module. An example could be if the cleaning module consists of a brushing head, and it is time for the brushing head to be replaced, the scoring parameter may be altered to reflect this.

In another embodiment of present invention, the oral care system includes an application software installed in the smartphone of the users. The game software sends the simplified brushing data to the application for the user (or the user's parental guardians) to track the performance of the user's brushing. The application can give rewards accordingly to the users.

In another embodiment of present invention, the software can communicate with similar software used by different users. All users can work or compete with each other to achieve better performance. The users can compete simultaneously, or separately, at different times. Each user can have their own oral care tool.

The software can send detailed brushing information to a cloud server. The cloud server has a database to store the brushing information of different users. This data can be used by individuals, parents, and care providers, such as dentists. The care providers can analyse the detailed brushing data to diagnosis potential oral problems of their patient. In one embodiment of present invention, a care provider (e.g., dentist) sends recommended instructions back to the game to change the game routine. The modified game instructs the user to brush more at the problematic teeth.

In another embodiment of present invention, the at least one sensor of the oral care tool includes a biochemical sensor that can detect the health condition of the user.

Figure 1:
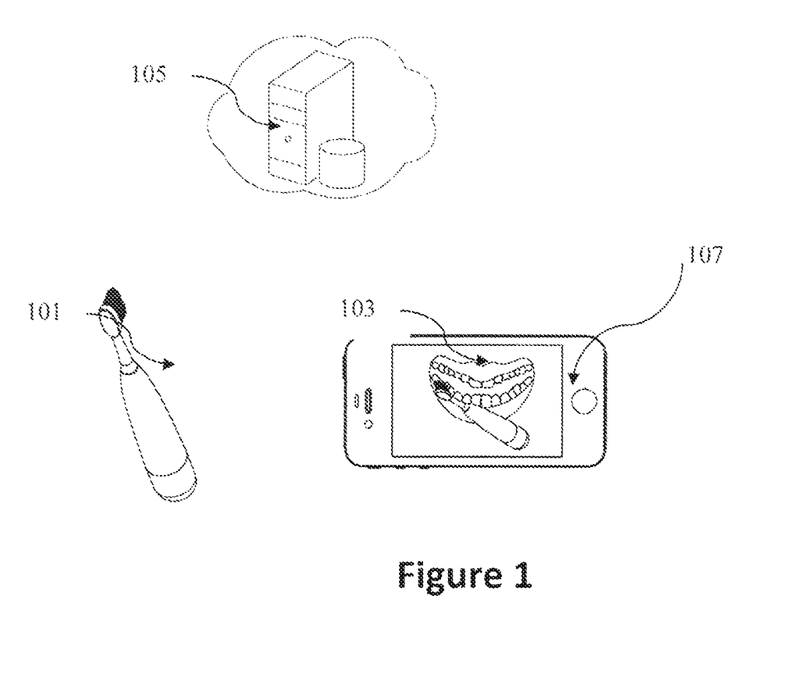
FIG. 1 is a schematic system diagram of an oral care system of the present invention.

Various modes are available for using the oral care systems of the invention. FIG. 1 shows an oral care system that includes: an oral care tool (101) comprising a cleaning module, a sensing module, and a communications module, and a first software application (103) that receives the data from the sensing module and reproduces a simulated image reflecting the results of brushing. FIG. 1 further illustrates a cloud server (105) that stores detailed brushing data for each user. In some embodiment, data stored on a server, such as a cloud server, constitutes a third subsystem of the oral care systems of the invention. A tooth brush used as an example of the oral care tool in Example 1 (and most of the implementation examples), but the principle of the present invention applies to other oral care tools, such as dental floss, water pic, etc. When users are brushing their teeth using the oral care tool, the sensor module detects the movement and positional information. The communications module receives the data from the sensor module and sends it to the first software application. Typically, the first software application is installed in a dedicated device or a general purpose device, like a smartphone or tablet. The first software application merges all data from the sensor and generates a simulated image (107) that reflects the brushing conditions and results of brushing. This data is optionally sent to and stored in the cloud server. The cloud server can send the data to a second software application installed in the user smartphone or mobile computing device for monitoring brushing. Care providers, such as parents, spouses, and dentists, can also access a user's brushing data. For care providers such as dentists, the data can be used for diagnostic purposes.

Figure 2:
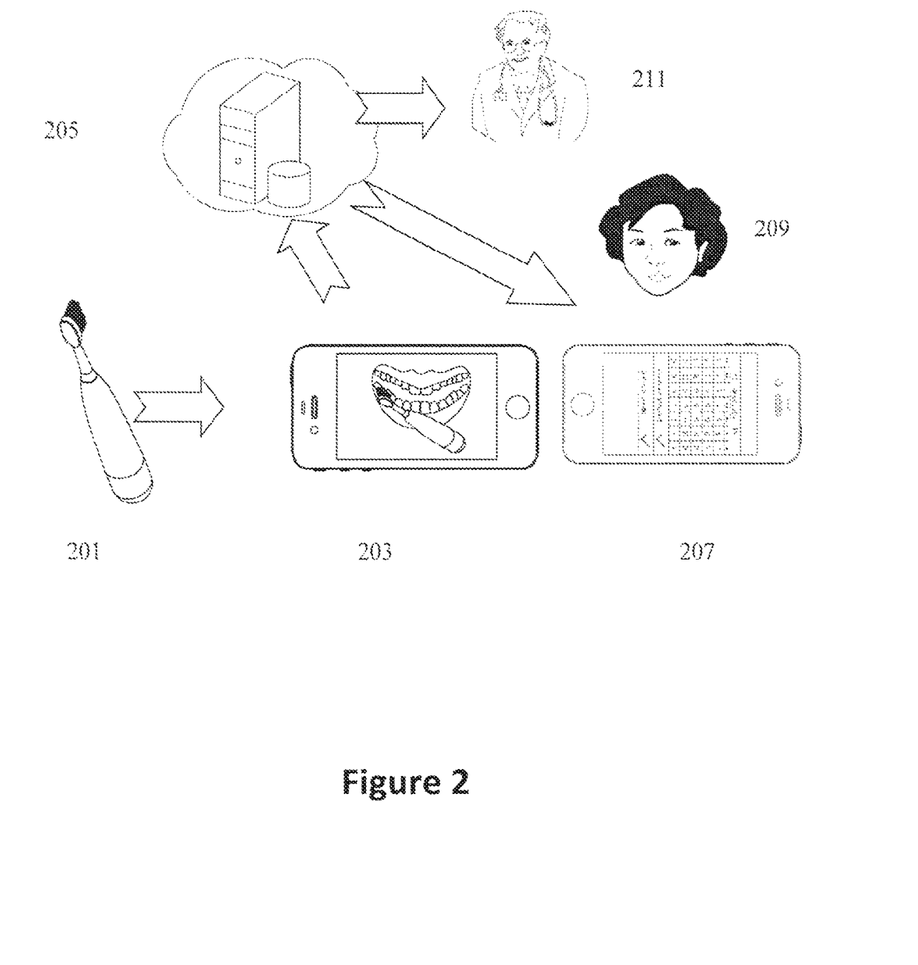
FIG. 2 is a schematic diagram of the data flow of the present invention.

FIG. 2 is a diagram of the flow of data that can result from use of the oral care systems of the present invention. The oral care tool 201 collects motion data and sends the data to first software application or game 203. The game 203 transmits data to the cloud server 205. The clouds server transmits data to the second software application in smartphone 207 for the user 209 to track the brushing activity. Care providers 211 have the access to the detailed data on the cloud server 205 for monitoring and diagnostic purposes. This is a simplified data flow. In another embodiment, the care provider and users can send data back to the first software application to alter the routine of the first software application, to improve the efficiency of brushing.

Figure 3:
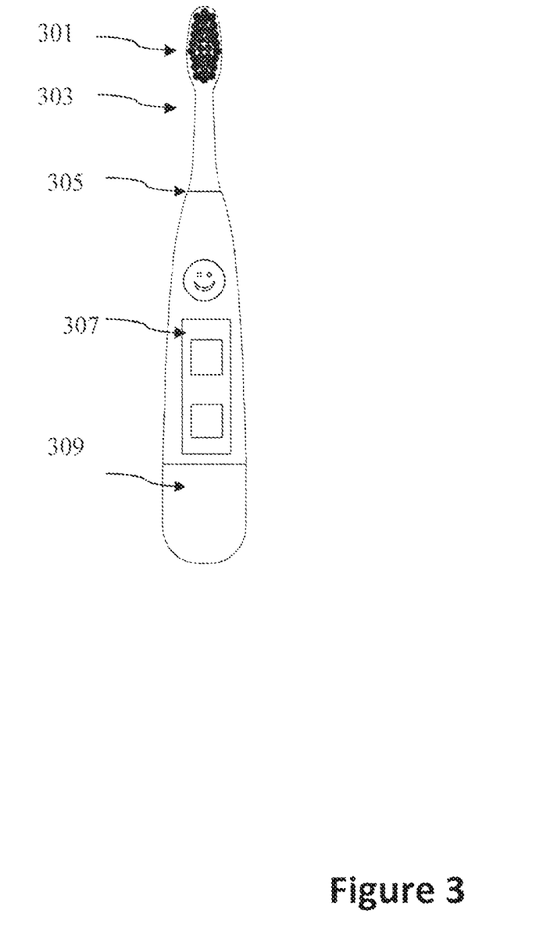
FIG. 3 is a schematic diagram of the brush of the present invention.

FIG. 3 shows a schematic diagram of the oral care device. It comprises all necessary parts for traditional function of a tooth brush, including bristles 301 on the cleaning module, a stem 303 on the cleaning module, and a body 305. The body 305 further comprises sensors 307 and wireless communication unit 309. The sensors 307 include but are not limited to, a gyroscope, magnetometer, accelerometer, temperature meter, and photo sensor. A timer is necessary to find the real brushing time. The timer should be physically located in the oral care system or use timer function in the portable computing device like a smartphone or a tablet. The gyroscope, accelerometers and magnetometer work alone or together to detect the actual rotation angles, i.e. Roll, Pitch and Yaw angle of the toothbrush. Roll and Pitch angle are used to determine the brushing surface and brushing angle of the teeth.

Figure 4:
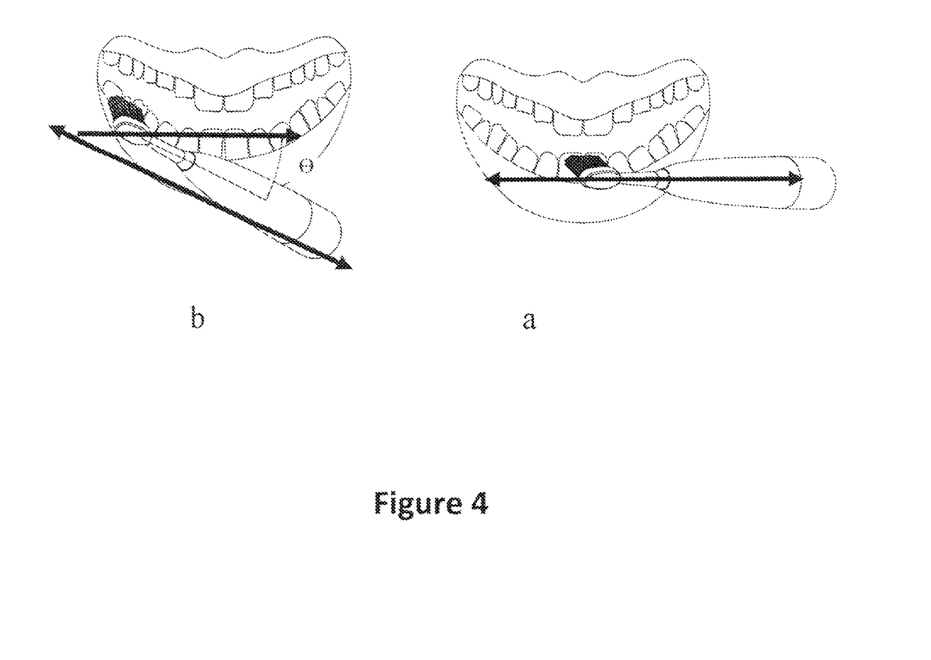
FIG. 4 is a schematic diagram of the brush of the present invention, wherein the Yaw angle of the brush is used to determine the position of brushing.

The rotation angle can be detected very accurately using current sensor technology but the absolute position is difficult to detect. In one embodiment of current patent, the Yaw angle of tooth brush is detected first. Because of the curvature of tooth, the Yaw angle has a one to one relationship with the position of the brush head. The Yaw angle is translated to absolute position of the brush head. The home position is the position when the incisors are being brushed. When Users are brushing the central Incisors, the Yaw angle of the brush is ZERO degrees as shown in FIG. 4 (*a*). When users are brushing the most inner Molar, the Yaw angle is a maximum angle, as shown in FIG. 4 (*b*). The Yaw angle of all other teeth can be interpolated mathematically, e.g., using a liner equation. By detecting the Yaw angle, the location of the teeth being brushed is detected.

In one embodiment, the Yaw angles of incisors and most inner molar of the user is detected and used to calibrate the oral care tool when the user uses the toothbrush the first time.

Figure 5:
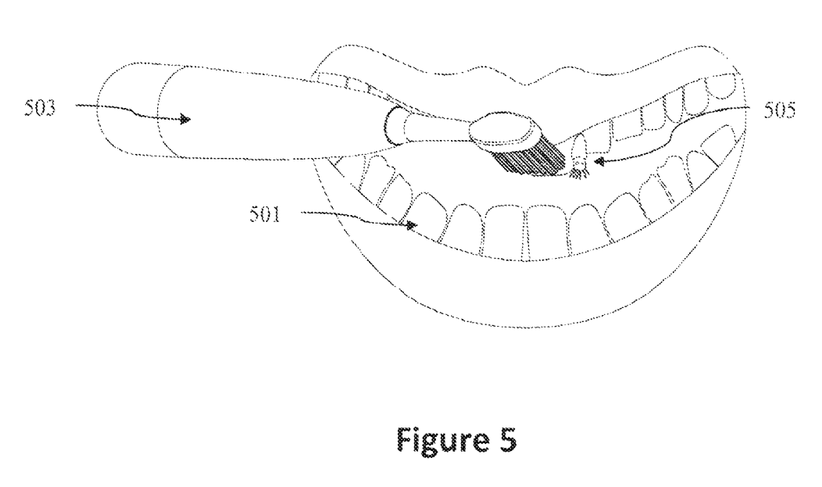
FIG. 5 is a game theme showing a simulated image of the teeth in the oral cavity and a simulated image of the brush of the present invention.

FIG. 5 shows an example of the first application software design. A simulated image of teeth within the oral cavity (501) is showed as a game background. The stored map of the user's mouth is mapped to the virtual image of teeth within the oral cavity 501. A virtual tooth brush (503) depicts the brushing movement based on the detected position of the real cleaning module within the oral cavity. A monster (505) is showed at different teeth and different surfaces as appropriate for good oral hygiene. The user brushes his/her teeth. The brush in the game follows the movement of the cleaning module on the oral care tool (i.e., the real tooth brush) to attack the monster. When the virtual brush collides with the monster in the game, the monster is destroyed. In this way the game can guide the usage of the oral care tool. When the brushing meets predetermined requirements, the monster in the game is killed and another monster or obstacle will appear at another location. The same processing is repeated until all teeth have been brushed properly.

Figure 6:
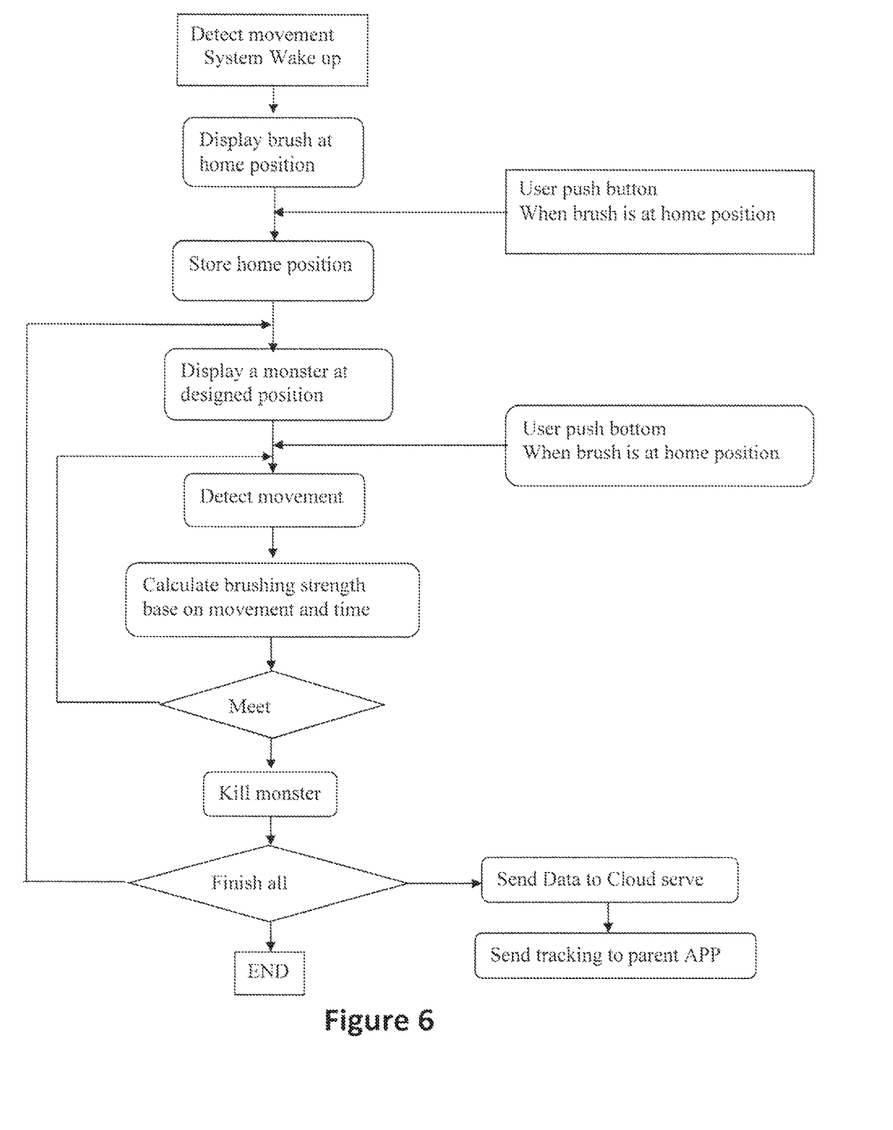
FIG. 6 is a flow chart of software routine of the present invention.

FIG. 6 shows a software flow chart. Those skilled in the art should appreciate that they may readily use the conception and the specific embodiment disclosed as a basis for modifying or designing other games for carrying out the same purposes of the present invention. Those skilled in the art should also realize that such equivalent constructions do not depart from the spirit and scope of the invention in its broadest form.

Figure 7:
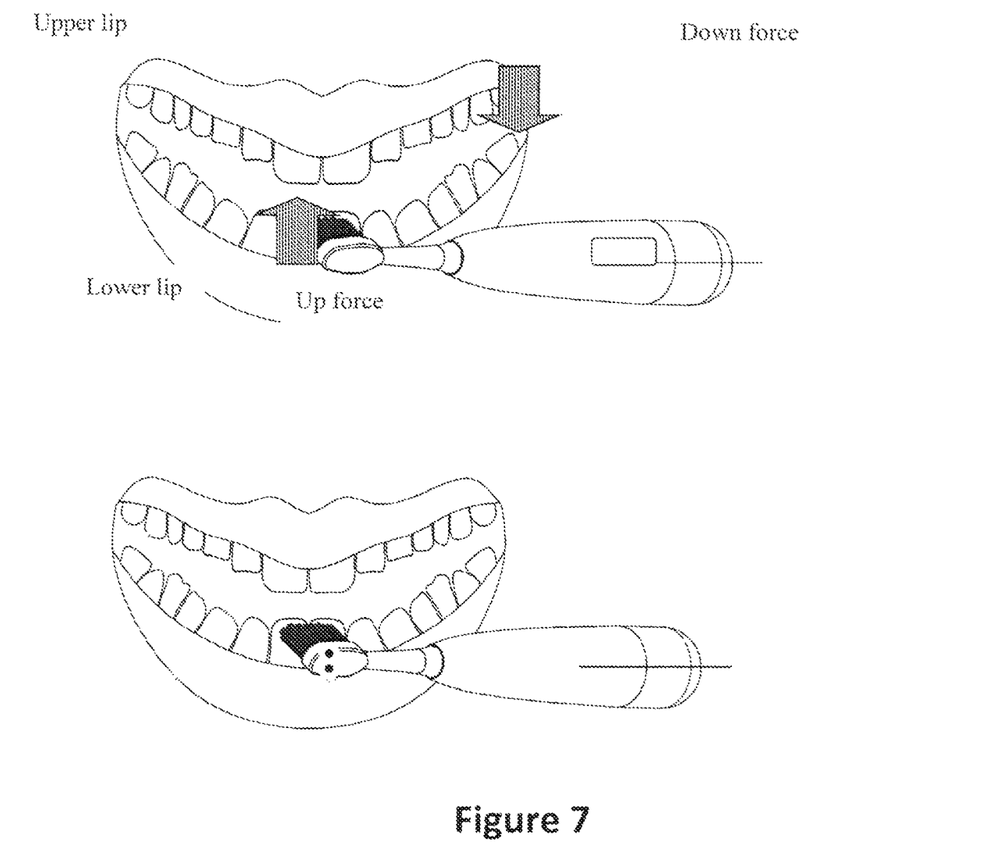
FIG. 7 is schematic diagram of method used in the present invention to determine the upper or lower teeth is brushed.

The upper teeth or lower teeth are also needed to be determined to properly reconstruct the brushing model. In one embodiment the monster is shown on the upper teeth, then the lower teeth. The user will follow the direction automatically to proper teeth. A clearly defined rotation gesture can determine if the cleaning module is in the upper or lower part of the mouth. In another embodiment, the tooth brush further comprises a pressure sensor/load sensor/force sensor. When the upper teeth are brushed, the force applied to brush is downward. When the lower teeth are brushed, the force is upward. The software determines which parts of teeth are brushed based on this information.

In another embodiment, the cleaning module further comprises two photo sensors on upper edge and bottom edge of brush head. When the upper teeth are brushed, the light on upper photo sensor is blocked by the lip. When the lower teeth are brushed, the light on bottom photo sensor is blocked. The software determines which part of teeth is brushed based on this information.

In another embodiment, the brush detects vertical acceleration. When users finish brushing upper teeth and move the brush head to lower teeth, the brush will detect vertical acceleration. The software uses this information to determine which teeth are being brushed. In another embodiment, the first software application detects the rotation orientation of the brush and infers whether the brush is on the upper or lower portion of the mouth.

In another embodiment of present invention, the lifetime of the brush head 301 is tracked by the first software application. The software keeps tracking the lifetime of the brush head and modifies the effectiveness of the weapon in the game. When the brush head has reached its lifetime, the weapon in the game loses its power therefore the user is informed to change the brush head.

What is claimed:

1. An oral care system comprising:
    an oral care tool comprising a cleaning module, a sensing module, and a communications module; and
    a first software application that can be run on a mobile computing device,
    wherein the cleaning module is designed to interface with teeth;
    wherein the sensing module comprises at least one sensor which generates data including 1) the position of the oral care tool within the oral cavity, 2) the orientation of the oral care tool to determine which face of the teeth the cleaning module is directed towards, and 3) the duration that the cleaning module is in each position and orientation within the oral cavity;
    wherein the at least one sensor includes an angular and rotational sensor that determines the position of the oral care tool, wherein a first angle is related to a most inner molar and a second angle is related to a central incisor;
    wherein the communications module receives the data from the sensing module, and transmits the data to a mobile computing device set up to run the first software application; and
    wherein the mobile computing device receives the data from the communications module on the oral care tool and reproduces a simulated image that reflects the result of brushing in real time.

2. The oral care system of claim 1, wherein the first software application directs the mobile computing device to upload the data with substantial accuracy from the oral care tool to a cloud server system.

3. The oral care system of claim 2, wherein the cloud server system provides access to the data with substantial accuracy to other software applications and/or users of the oral care system.

4. The oral care system of claim 3, wherein the data accessible from the cloud storage system with substantial accuracy can be used to track oral care and/or aid dental diagnosis.

5. The oral care system of claim 1, wherein the first software application adjusts its routines in an automated manner or in response to manual input.

6. The oral care system of claim 1, wherein the at least one sensor includes an accelerometer, wherein acceleration data from the accelerometer can be integrated by hardware or software to determine the position of the oral care tool.

7. The oral care system of claim 1, wherein the at least one sensor includes a load sensor or strain gauge that can determine the direction of load force.

8. The oral care system of claim 1, wherein the cleaning module includes a toothbrush, floss, a gum instrument, a water flossing tool, or any combination thereof.

9. The oral care system of claim 1, wherein the simulated image includes a visual representation of teeth surfaces within the oral cavity or a game theme wherein positions within the simulated image have one to one correlation with teeth surfaces within the oral cavity.

10. The oral care system of claim 1, wherein the simulated image changes its color the based on the data from the sensors.

11. The oral care system of claim 1, further comprising a second software application capable of running on the device running the first software application or another device, wherein the second software application allows tracking of the performance of and usage of the oral care tool.

12. The oral care system of claim 1, wherein the first software application allows different users to compete with one another.

13. The oral care system of claim 1, wherein the first software application displays a representation of the oral care tool at a desired orientation to guide the user.

14. The oral care system of claim 1 wherein the first software application compares a detected brushing pattern with a desired brushing pattern to give a score based on the difference between them.

15. The oral care system of claim 1, wherein the first software application provides a visual representation of the oral care tool and tracks total usage of the cleaning module, and wherein the visual representation of the oral care tool changes with increasing usage.

16. The oral care system of claim 1, wherein the first software application tracks total usage of the cleaning module, and wherein a scoring parameter within the first software application is altered with increasing usage.

17. An oral care system comprising:
    an oral care tool comprising a cleaning module, a sensing module, and a communications module; and
    a first software application that can be run on a mobile computing device,
    wherein the cleaning module is designed to interface with teeth;
    wherein the sensing module comprises at least one sensor which generates data including 1) the position of the oral care tool within the oral cavity, 2) the orientation of the oral care tool to determine which face of the teeth the cleaning module is directed towards, and 3) the duration that the cleaning module is in each position and orientation within the oral cavity;
    wherein the at least one sensor includes a photo sensor that determines the position of the oral care tool, wherein a first level of light is related to the central incisors, and a second level of light is related to the most inner molar;
    wherein the communications module receives the data from the sensing module, and transmits the data to a mobile computing device set up to run the first software application; and
    wherein the mobile computing device receives the data from the communications module on the oral care tool and reproduces a simulated image that reflects the result of brushing in real time.

18. A dental diagnosis system comprising:
    an oral care tool comprising a cleaning module, a sensing module, and a communications module; and
    a first software application that can be run on a mobile computing device,
    wherein the cleaning module is designed to interface with teeth;
    wherein the sensing module comprises at least one sensor which generates data including 1) the position of the oral care tool in the oral cavity, 2) the orientation of the oral care tool to determine which face of the teeth the oral care tool is directed towards, and 3) the duration that the cleaning module is in each position and orientation within the oral cavity;
    wherein the at least one sensor includes an angular and rotational sensor that determines the position of the oral care tool, wherein a first angle is related to a most inner molar and a second angle is related to a central incisor;

wherein the communications module receives the data from the sensing module, and transmits the data to a mobile computing device set up to run the first software application;

wherein the mobile computing device receives the data from the communications module on the oral care tool and reproduces a simulated image that reflects the result of brushing in real time; and wherein the first software application directs the mobile computing device to upload the data from the oral care tool to a cloud storage system.

19. The dental diagnosis system of claim 18, wherein one or more requirements of a care provider are provided to the first software application, and wherein the one or more requirements change the operation of the first software application accordingly.

* * * * *